United States Patent [19]

Knoll et al.

[11] Patent Number: 4,921,861

[45] Date of Patent: *May 1, 1990

[54] PHARMACEUTICAL COMPOSITIONS

[75] Inventors: József Knoll; né Simonyi Budai; Edit Berényi né Poldermann; Ildikó Miklya; Márton Fekete; Gabriella Zsilla; Berta Knoll; Attila Mándi; Lujza Petöcz; István Gyertyán; István Gacsályi, all of Budapest, Hungary

[73] Assignee: BASF Aktiengesellschaft, Ludwigshafen, Fed. Rep. of Germany

[*] Notice: The portion of the term of this patent subsequent to May 1, 2007 has been disclaimed.

[21] Appl. No.: 185,049

[22] Filed: Apr. 22, 1988

[30] Foreign Application Priority Data

Apr. 24, 1987 [HU] Hungary ............................... 1777/87

[51] Int. Cl.$^5$ .................... C07D 215/36; A61K 31/47
[52] U.S. Cl. ...................................... 514/312; 546/155
[58] Field of Search ......................... 514/312; 546/153

[56] References Cited

U.S. PATENT DOCUMENTS 4,788,204  11/1988  Benquides et al. ................. 514/312

Primary Examiner—William R. Dixon, Jr.
Assistant Examiner—Miriam Sohn
Attorney, Agent, or Firm—Keil & Weinkauf

[57] ABSTRACT

The 3-amino-4-ethylthio-quinoline of the Formula I

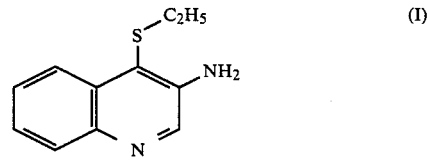

and pharmaceutically acceptable acid addition salts thereof possess useful therapeutical properties. They exhibit a potent and highly selective anxiolytic and narcosis potentiating effect and are devoid of sedative and anti-convulsive effect. Consequently, the invention relates to pharmaceutical compositions comprising the compound of Formula I or a salt thereof as active agent.

The invention also relates to a new and improved process for the preparation of the compound of Formula I.

4 Claims, No Drawings

PHARMACEUTICAL COMPOSITIONS

The invention relates to pharmaceutical compositions comprising 3-amino-4-ethylthio-quinoline of the Formula I

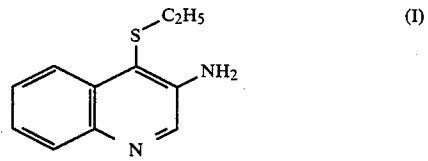

or a pharmaceutically acceptable acid addition salt thereof and a process for the preparation of the said active ingredient.

The compound 3-amino-4-ethylthio-quinoline of the Formula I has been described in prior art [Hiroyuki Sawanishi et al.: "Heterocycles" 22/7, 1501–1504 (1984)]. According to the said article 3-amino-4-ethylthio-quinoline is prepared by subjecting 3-azido-quinoline to photolysis or thermolysis in the presence of ethane thiol. The authors are, however, completely silent in disclosing any biological effect of the compound of Formula I.

It has been found in a surprising manner that 3-amino-4-ethylthio-quinoline possesses valuable therapeutical properties and exhibits a particularly potent anxiolytic and narcosis potentiating effect.

The particular advantage of 3-amino-4-ethylthio-quinoline resides in the fact that it shows a highly selective anxiolytic effect and is devoid of sedative and anti-convulsive effects.

The pharmacological activity of 3-amino-4-ethylthio-quinoline is substantiated by the following tests. As test compound 3-amino-4-ethylthio-quinoline-hydrochloride (referred to further as "Compound A") is used.

The toxicity data are as follows:
oral $LD_{50}$ (on rats) 420 mg/kg;
s.c. $LD_{50}$ (on rats) 320 mg/kg.

In the well-known "hot-plate" test Compound A shows the following activity:
s.c. $ED_{50}$=40 mg/kg;
oral $ED_{50}$=49 mg/kg.

Compound A is ineffective in the algolytic test (on rats).

The narcosis potentiating effect of Compound A (on rats) is very strong if inactine is used. The dose of Compound A which causes a five-fold prolongation of the inactine narcosis time amounts to $ED_{500}$ s.c.=3.5 mg/kg and $ED_{500}$ p.o.=3.4 mg/kg, respectively. Since Compound A prolongs the hexobarbital narcosis time to a much weaker extent and it does not lengthen the narcosis time of a non-barbiturate phenyclidine derivative (i.e. calypsol), it is likely that the prolongation of inactine narcosis time is caused by a metabolic interaction and not by a general central effect.

Compound A shows no spasmolytic effect on spasms induced by tetracor when administered in a dose of 25 and 100 mg/kg p.o., respectively.

In the modified jumping test Compound A does not inhibit the unconditioned avoidance reflex when administered in a dose of 50 and 100 mg p.o., respectively.

In a dose of 50 and 100 mg/kg p.o., respectively, Compound A inhibits the spontaneous motility (on rats) moderately in a dose-independant manner. In a dose of 25 mg/kg Compound A is inactive.

In the one-way conditioned avoidance test (screening test I) Compound A shows a very weak inhibiting effect even if administered in a dose of 100 mg/kg p.o.

In the shuttle box (two-way conditioned avoidance reflex) Compound A inhibits learning ability on rats significantly if administered in a 100 mg/kg p.o. dose.

Compound A does not influence metabolism on rats in a dose of 100 mg/kg p.o.

Anxiolytic and sedative effects are studied according to the following conflict test. The results are summarized in Table I. Compound A significantly increases water consumption punished by trains of electric shock already in a dose of 2.5 γ/kg, i.e. it is an extremely active anxiolytic agent. On the other hand, sedative effect can be observed but in a dose of 25 mg/kg. Thus the ratio of the anxiolytic and sedative doses amounts to 25,000:2.5=10,000. The same value of chlordiazepoxide is 10:0.1=100. It appears that in the case of Compound A the dissociation between the sedative and anxiolytic doses is extremely high.

Compound A displaces diazepame from the benzodiazepine receptors.

TABLE 1

| Compound A s.c. 0.5 ml/100 g 0.5 hour (distilled water) | "Conflict test" | | | |
|---|---|---|---|---|
| | With electric current | | Without electric current | |
| | water uptake (ml) | No. of animals | water uptake (ml) | No. of animals |
| 2.5 γ/kg | 3.4 ± 0.43$^x$ | 10 | — | — |
| 5 γ/kg | 4.1 ± 0.66$^{xxx}$ | 10 | — | — |
| 10 γ/kg | 2.7 ± 0.33 | 10 | — | — |
| 25 γ/kg | 2.8 ± 0.38 | 10 | — | — |
| 0.25 mg/kg | 3.3 ± 0.45$^x$ | 10 | 6.1 ± 0.46 | 10 |
| 5 mg/kg | — | — | 7.2 ± 0.37 | 10 |
| 10 mg/kg | — | — | 6.9 ± 0.43 | 10 |
| 25 mg/kg | — | — | 3.4 ± 0.60$^{xx}$ | 7 |
| Control (distilled water) s.c. 0.5 mlg/100 g 0.5 hour | 2.3 ± 0.19 | 40 | 6.4 ± 0.57 | 15 |

$^x p < 0.05$
$^{xx} p < 0.01$
$^{xxx} p < 0.001$

Measurement of the anti-anxiety versus sedative effect of Compound A

The essential strategy for measuring the anti-anxiety effect of a drug is to check its activity in a conflict situation. We elicit a rewarded response, then suppress that response by punishing it when it occurs and the anti-anxiety effect is measured by the drug-induced increase in punished responding, whereas the sedative effect is measured by the drug-induced decrease of unpunished responding.

A rat, deprived of food for 96 hours and supplied with water ad libitum, drinks about 7 ml water during the 4th day of food deprivation, but needs 35 ml water daily when supplied with dry food [for review see Knoll, J. J., Neural Transm. 59, 163–194 (1984)]. This means that when we circuit the drinking tube and the grid floor of the cage and the rat is regularly shocked by trying to drink, the very hungry animal, which cannot eat without drinking, is maximally forced to overcome the hindrance. This is a sensitive test to check the anti-anxiety effect of a compound.

Male CFY rats, weighing 230–250 g, fed with standard food pellets and supplied with tap water ad libitum, were kept under controlled standard environmental conditions (room temperature between 22°-24° C.) in groups of ten for two weeks until used in the experiment. The rats kept in single cages during starvation were deprived of food for 96 hours and supplied with tap water ad libitum before the experiment.

Only those animals which did not lose more than 80 g body weight during the starvation period were selected for the experiment. In our test, based on calculations from the changes in 550 male rats deprived of food for 96 hours, the average loss of body weight was found to be 66 g.

Another aspect of the selection of the animals for the experiment was their visible physical fitness and normal activity after starvation. Less than 10 percent of the rats were excluded from the experiment because of insufficient physical fitness.

A clear Plexiglass box (39×27×12 cm) with a stainless-steel grid floor supplied with a tray for the food pellets and with a drinking tube was used for the experiment. The grid floor, the drinking tube and an electric stimulator (Grass S48) were connected and electric shocks in this circuit were delivered for 10 s duration with 20 s intervals. The parameters of the current (100V; 25 ohm; 7.5 ms; 5 Hz) were empirically selected using those electric shocks which inhibited the water consumption of the very hungry rats to one third of the control (unpunished) level.

The rats spend one hour in the apparatus after 96 hours of food deprivation. The very hungry rats eat 5–6 g of food pellets during the first hour of the feeding period after the long starvation. The water consumption of the hungry rats during the first hour of the feeding period was measured in groups of rats without punishment and was found to be 6–7 ml. In the punished situation the consumption was reduced to less than 3 ml.

The drugs were administered parenterally in doses of 0.5 ml/100 g body weight. We refrained from the oral administration of the compounds because of the long term food deprivation.

According to a further aspect of the present invention there is provided a new and improved process for the preparation of 3-amino-4-ethylthio-quinoline.

According to the article "Heterocycles" 22/7 1501–1504 (1984) 3-amino-4-ethylthio-quinoline is prepared by subjecting 3-azido-quinoline to photolysis or thermolysis in the presence of ethane thiol. This process is accompanied by several serious drawbacks. The process is but of theoretical value and is unsuitable for industrial scale manufacture. The photochemical reaction can be carried out only on small scale and in special equipments. The starting material is explosive and the reactant is very toxic.

It is an object of the present invention to elaborate an industrial scale process for the preparation of 3-amino-4-ethylthio-quinoline which overcomes the disadvantages of the known method.

According to the present invention 3-amino-4-ethylthio-quinoline of the Formula I and pharmaceutically acceptable acid addition salts thereof may be prepared by (a) ethylating 3-amino-4-quinoline-thiol of the Formula II;

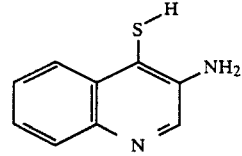

or (b) ethylating 3-nitro-4-quinoline-thiol of the Formula III

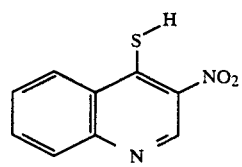

and reducing the 4-ethylthio-3-nitro-quinoline of the Formula IV

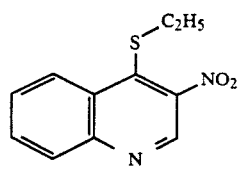

thus obtained; or (c) reacting 4-chloro-3-nitro-quinoline of the Formula V

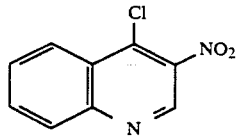

with an alkali ethane thiolate and reducing the 4-ethylthio-3-nitro-quinoline of the Formula IV thus obtained; and, if desired, converting the compound of the Formula I into a pharmaceutically acceptable acid addition salt thereof.

According to method (a) the ethylation of 3-amino-4-quinoline-thiol of the Formula II is carried out by methods known per se. As ethylating agent e.g. ethyl halides, diethyl sulfate or ethyl aryl sulfonates can be used in the presence of a base. One may proceed preferably by accomplishing ethylation with diethyl sulfate or ethyl benzene sulfonate in the presence of an alkali hydroxide (preferably sodium or potassium hydroxide). Ethylation can be carried out at a temperature between 20° C. and 160° C., preferably under heating. One may particularly preferably work at the boiling point of the reaction mixture. Ethylation may be advantageously carried out in a polar solvent (e.g. in aqueous medium). The compound of the Formula I thus obtained can be isolated from the reaction mixture by known methods (e.g. filtration, evaporation or extraction).

According to method (b) 3-nitro-4-quinoline-thiol of the Formula III is ethylated by methods known per se e.g. in an analogous manner to method (a). The 4-ethylthio-3-nitro-quinoline of the Formula IV can be reduced to the compound of the Formula I by methods known per se. Reduction may be preferably accomplished with the aid of an alkali sulfide (preferably sodium sulfide) in aqueous medium. The reaction may be preferably carried out under heating, particularly under reflux. The compound of the Formula I thus obtained may be isolated from the reaction mixture by known methods.

According to method (c) 4-chloro-3-nitro-quinoline of the Formula V is reacted with an alkali ethane thiolate (preferably sodium ethane thiolate). The reaction may be accomplished in an organic solvent, optionally in the presence of water. The reaction may be carried out at room temperature or under slight warming. The 4-ethylthio-3-nitro-quinoline of the Formula IV thus obtained can be reduced to the desired compound of the Formula I by known methods, i.e. as described in connection with method (b).

The 3-amino-4-ethylthio-quinoline of the Formula I can be converted into a pharmaceutically acceptable acid addition salt. Salt formation can be carried out by methods known per se by reacting the base of the Formula I with a molar equivalent amount of the corresponding acid in an inert organic solvent. For salt formation pharmaceutically acceptable inorganic acids (e.g. hydrochloric acid, hydrogen bromide, sulfuric acid, phosphoric acid etc.) or strong organic acids (e.g. ethane sulfonic acid etc.) may be used.

The starting materials of the Formulae II, III and IV are partly known [Bachman et al: J. Am. Chem. Soc. 69, 365–71 (1947)] or can be prepared in a manner analogous to known compounds.

The advantages of the process of the present invention can be summarized as follows:
the process is readily feasible on industrial scale, too;
the yields are high;
readily available and cheap starting materials are used.

According to a further feature of the present invention there are provided pharmaceutical compositions comprising a compound of the Formula I or a pharmaceutically acceptable acid addition salt thereof as active agent admixture with suitable inert solid or liquid pharmaceutical carriers.

The active ingredient can be finished in forms suitable for oral (e.g. tablet, pill, coated pill, dragée, hard or soft gelatine capsule, solution, emulsion, suspension), parenteral (e.g. injectable solution) or rectal (e.g. suppository) application.

The pharmaceutical compositions of the present invention can be prepared by methods of the pharmaceutical industry known per se. The compound of the Formula I or a pharmaceutically acceptable acid addition salt thereof is admixed with inert, solid or liquid, organic or inorganic pharmaceutical carriers and/or excipients and the mixture is brought into a galenic form.

Tablets, pills, coated pills, dragées and hard gelatine capsules may comprise as carrier e.g. lactose, maize starch, potato starch, talc, magnesium carbonate, magnesium stearate, calcium carbonate, stearic acid or salts thereof etc. The soft gelatine capsules may comprise as carrier e.g. vegetable oils, fats, waxes or polyols of suitable consistence etc. In the preparation of solutions or syrups e.g. water, polyols, polyethylene glycol, saccharose or glucose may be used as carrier. The injectable solutions may comprise e.g. water, alcohols, polyols, glycerol or vegetable oils as carrier.

In the preparation of suppositories e.g. oils, waxes, fats and polyols of suitable consistence may be used as carrier.

The pharmaceutical compositions of the present invention may also comprise conventional auxiliary agents generally used in pharmaceutical industry (e.g. wetting, dispersing, conserving, emulsifying agents, dyes, sweetening agents, aroma materials, salts for modifying the osmotic pressure, buffers etc.). The pharmaceutical compositions of the present invention may comprise further therapeutically valuable materials, too.

It is preferred to use the compounds of the general Formula I in forms suitable for oral application, particularly as tablets or capsules. It is particularly preferred to use tablets or capsules having an active ingredient content of from about 2.5 mg to about 50 mg as dosage forms.

The daily dose of the compound of the Formula I may vary between wide ranges and depends on various factors (e.g. efficiency of the active ingredient, condition and age of the patient, severeness of the disease etc.). The daily oral dose may be approximately about 1–300 mg while the daily parenteral dose generally amounts to about 0.5–150 mg. It is to be emphasized that the above dose intervals are but of an informative character and the actual dose may be lower or higher as well and is always determined by the physician.

According to a further aspect of the present invention there is provided the use of a compound of the Formula I or a pharmaceutically acceptable acid addition salt thereof for the preparation of pharmaceutical compositions having anxiolytic and narcosis potentiating effect.

According to a still further aspect of the present invention there is provided a method of anxiolytic treatment which comprises administering to the patient an effective dose of a compound of general Formula I or a pharmaceutically acceptable acid addition salt thereof.

Further details of the present invention are to be found in the following Examples without limiting the scope of protection to the said Examples.

EXAMPLE 1

17.62 g (0.1 mole) of 3-amino-4-quinoline-thiol are dissolved in 50 ml of a 2 molar sodium hydroxide solution whereupon some sodium pyrosulfite crystals are added to the solution. At a temperature below 60° C. 22 g (0.14 mole) of ethyl iodide are added dropwise. The reaction mixture is stirred at 60° C., the product is extracted with chloroform, clarified with activated charcoal and evaporated. Thus 17.3 g of 3-amino-4-ethylthio-quinoline are obtained, yield 85%, b. p.: 147° C./26.6 N.m$^{-2}$.

The yellow oily base thus obtained is converted into the hydrochloride in ethyl acetate by adding ethanol containing hydrochloric acid. Thus 20.0 g of 3-amino-4-ethylthio-quinoline-hydrochloride are obtained, yield 98%, m.p.: 228°–230° C. (from methanol).

EXAMPLE 2

17.62 g (0.1 mole) of 3-amino-4-quinoline-thiol are dissolved in 125 ml of a 2 molar sodium hydroxide solution whereupon 23.30 g (0.125 mole) of ethyl benzene sulfonate are added. The reaction mixture is heated to boiling for 2 hours, the product formed is extracted with chloroform and to the chloroform extract alcohol containing hydrogen chloride is added. Thus 21.0 g of 3-amino-4-ethylthio-quinoline-hydrochloride are obtained, yield 87%, m.p.: 228°–230° C. (from methanol).

EXAMPLE 3

20.52 g (0.1 mole) of 3-nitro-4-quinoline-thiol are taken up in 150 ml of a molar sodium hydroxide solution. After addition of some sodium pyrosulfite crystals 23.3 g (0.15 mole) of ethyl iodide are added at 60° C. After the reaction has been completed the product formed is extracted with dichloro methane and the extract is evaporated. The 4-ethylthio-3-nitro-quinoline thus obtained (18.6 g) is dissolved in alcohol, an aqueous sodium sulfide solution is added, the reaction mixture is refluxed and then diluted with water. The product is extracted with dichloro methane, the extract is clarified and evaporated. From the residue (13.6 g, yield 83.5%) the hydrochloride is formed by usual methods. Thus 14.0 g of 3-amino-4-ethylthio-quinoline-hydrochloride are obtained. The product is identical with the compound prepared according to Example 1 or 2.

EXAMPLE 4

To a chloroform solution of 20.86 g (0.1 mole) of 4-chloro-3-nitro-quinoline a solution of 16.8 g of sodium ethane thiolate formed with a mixture of methanol and water is added at a temperature below 20° C. After a post-reaction period the reaction mixture is extracted with alkaline water several times and the chloroform solution is evaporated. The 4-ethylthio-3-nitro-quinoline thus obtained is reduced and worked up as described in Example 3. Thus 3-amino-4-ethylthio-quinoline-hydrochloride is obtained.

EXAMPLE 5

Tablets having the following composition are prepared:

| Component | Amount, mg/tablet |
| --- | --- |
| 3-Amino-4-ethylthio-quinoline--hydrochloride | 25.0 |
| Maize starch | 97.0 |
| Polyvinyl pyrrolidone | 175.0 |
| Magnesium stearate | 3.0 |
| Total weight | 300.0 |

A mixture of the active ingredient and maize starch is wetted with a 10-15% aqueous polyvinyl pyrrolidone solution, the mixture is granulated and dried at 40°-45° C. The granules thus obtained are thoroughly dried, admixed with magnesium stearate and pressed to tablets.

EXAMPLE 6

Capsules of the following composition are prepared by methods of pharmaceutical industry known per se:

| Component | Amount, mg/capsule |
| --- | --- |
| 3-Amino-4-ethylthio-quinoline-hydrochloride | 20.0 |
| Lactose | 60.0 |
| Maize starch | 17.0 |
| Talc | 2.0 |
| Magnesium stearate | 1.0 |
| Total weight | 100.0 |

What we claim is:

1. A pharmaceutical composition having anxiolytic and narcosis potentiating effect comprising as active ingredient 3-amino-4-ethylthio-quinoline of the formula I

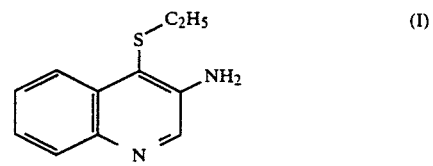

or a pharmaceutically acceptable acid addition salt thereof in admixture with suitable inert solid or liquid pharmaceutical carriers.

2. A pharmaceutical composition as defined in claim 1, wherein the active ingredient is 3-amino-4-ethylthio-quinoline-hydrochloride.

3. A method of treating a patient for anxiety which comprises: administrating to a patient in need thereof an effective amount of a composition as defined in claim 1.

4. A method of treating a patient for anxiety which comprises: administrating to a patient in need thereof an effective amount of a composition as defined in claim 3.

* * * * *